United States Patent [19]
Mougin et al.

[11] Patent Number: 5,961,989
[45] Date of Patent: Oct. 5, 1999

[54] COSMETIC OR DERMATOLOGICAL COMPOSITION IN AN AQUEOUS MEDIUM COMPRISING A FILM-FORMING OLIGOMER AND RIGID, NON-FILM-FORMING NANOMETRIC PARTICLES AND USES THEREOF

[75] Inventors: Nathalie Mougin, Paris; Jean Mondet, Aulnay Sous Bois; Alain Franbourg, Paris; Daniel Bauer, Le Raincy; Henri Samain, Bièvres, all of France

[73] Assignee: L'Oreal, Paris, France

[21] Appl. No.: 08/722,919

[22] Filed: Sep. 23, 1996

[30] Foreign Application Priority Data

Sep. 21, 1995 [FR] France ................................. 95 11109
Oct. 3, 1995 [FR] France ................................. 95 11615

[51] Int. Cl.$^6$ ........................................................ A61K 7/48
[52] U.S. Cl. ............................ 424/401; 424/61; 424/70.1; 424/70.7; 424/70.11; 424/70.15; 424/70.16; 424/70.17; 424/47
[58] Field of Search .................................. 424/401, 70.1, 424/70.11, 70.15, 70.16, 70.17, 61, 70.7, 47; 514/844

[56] References Cited

U.S. PATENT DOCUMENTS

| 3,821,372 | 6/1974 | Vanilerberghe et al. . |
|---|---|---|
| 3,928,224 | 12/1975 | Vanlerberghe et al. . |
| 3,966,398 | 6/1976 | Vanlerberghe et al. . |
| 4,087,466 | 5/1978 | Vanlerberghe et al. . |
| 4,871,536 | 10/1989 | Arraudeau et al. . |
| 5,660,820 | 8/1997 | Mondet et al. ....................... 424/70.16 |

FOREIGN PATENT DOCUMENTS

| 0 214 626 | 9/1986 | European Pat. Off. . |
|---|---|---|
| 0 288 012 | 4/1988 | European Pat. Off. . |
| 0 320 218 | 12/1988 | European Pat. Off. . |
| 0 628 304 | 6/1994 | European Pat. Off. . |
| 2 091 516 | 5/1971 | France . |
| 2 528 699 | 6/1983 | France . |

*Primary Examiner*—Jyothsna Venkat
*Attorney, Agent, or Firm*—Finnegan, Farabow, Garrett & Dunner, L.L.P.

[57] ABSTRACT

Cosmetic or dermatological compositions comprising in a cosmetically acceptable medium (A) at least one film-forming oligomer having a molecular weight, measured by steric exclusion chromatography, of less than or equal to 50,000, said at least one film-forming oligomer being soluble or dispersible in said cosmetically acceptable aqueous medium; and (B) rigid, non-film-forming particles of average size less than or equal to 1 $\mu$m, said rigid, non-film-forming particles being dispersed in said cosmetically acceptable aqueous medium, wherein the compositions may be used, for example, as product bases for maintaining the hairstyle, as products for coating the eyelashes and the eyebrows or as nail make-up and/or care products.

58 Claims, No Drawings

COSMETIC OR DERMATOLOGICAL COMPOSITION IN AN AQUEOUS MEDIUM COMPRISING A FILM-FORMING OLIGOMER AND RIGID, NON-FILM-FORMING NANOMETRIC PARTICLES AND USES THEREOF

The present invention relates to cosmetic or dermatological compositions comprising, in a cosmetically acceptable aqueous medium, at least one film-forming oligomer which is soluble or dispersible in the said medium, and at least one type of rigid, non-film-forming nanometric, i.e., average particle size of less than or equal to 1 μm, particles dispersed in the said medium, as well as to their uses in the cosmetics or dermopharmacy field, in particular in products for maintaining the hairstyle, products for coating the eyelashes and eyebrows, and nail make-up and/or care products.

Film-forming polymers that are soluble in aqueous and aqueous-alcoholic media, such as polyvinylpyrrolidone, vinylpyrrolidone/vinyl acetate copolymers, vinyl acetate/crotonic acid copolymers, and anionic or amphoteric acrylic resins are commonly used in hair fixing products, mascaras or nail make-up and/or care products.

The hair fixing products most widely found on the cosmetics market are spray compositions comprising a solution, usually an aqueous-alcoholic solution, and a film-forming polymer which is soluble in water and in alcohol, such as those mentioned above, as a mixture with various cosmetic adjuvants. This solution is generally packaged either in a suitable aerosol container placed under pressure by means of a propellant gas, or in a pump-dispenser.

For a certain number of years, special interest has developed in aerosol lacquers or pump-dispensers containing high water concentrations with a high film-forming polymer "solids content".

Throughout this description, the expression aerosol or pump-dispenser with a "high solids content" of lacquering product will be understood to refer to any aqueous formulation packaged in the form of an aerosol or pump-dispenser containing more than 5% solids by weight of lacquering product relative to the total weight of the said formulation.

On the one hand, it is sought to decrease the concentrations of compounds that are volatile at atmospheric pressure, referred to as VOC (volatile organic compound), present in spray compositions in the form of an aerosol or a pump-dispenser. The reason for this is that the use of alcohol, alone or as a mixture with a small amount of water, and the use of propellant gases may have certain drawbacks such as increasing flammability or environmental pollution.

VOCs are mainly propellant gases such as hydrocarbons or dimethyl ether (DME) and solvents such as ethanol.

On the other hand, it is sought to reduce the drying time of the sprayed product and to increase its lacquering power after it is sprayed on the hair. The use of water-soluble film-forming polymers in aerosols or pump-dispensers with high water concentrations, in particular in water/ethanol/dimethyl ether spray systems having a maximum VOC content of 55%, requires higher concentrations of polymer solids compared with those used in organic spray systems (100% VOC) in order to obtain satisfactory fixing powers and drying times.

The reason for this is that the increase in water concentration in the aerosol or pump-dispenser packagings leads to a large decrease in lacquering power as well as to much longer drying times.

The film-forming polymers usually used in compositions of this type have molecular weights, measured by steric exclusion chromatography, which are generally greater than 50,000 and more preferably greater than 100,000.

The increase in their concentration in aerosol lacquers or pump-dispensers with high water contents leads to excessively high viscosities, such that the product can no longer be satisfactorily sprayed from the aerosol or the pump-dispenser.

To overcome these problems of viscosity, one solution would consist in using film-forming oligomers which are soluble or dispersible in the medium of the composition to be sprayed, affording a low viscosity. Presently, most of the oligomers, with a molecular weight of less than 50,000, used in products to maintain the hair have mechanical properties that are insufficient to obtain a satisfactory lacquering power, even at high concentrations.

The inventors have discovered, surprisingly, that by combining rigid, non-film-forming nanometric particles with film-forming oligomers with a molecular weight of less than 50,000, that are soluble or dispersible in aqueous media, aerosol lacquers or pump-dispensers may be made with a high lacquering agent solids content, having good diffusion on application, a good lacquering power and a good rate of drying. This combination is most particularly suited to aerosol hair compositions with a "high solids content" of the water/ethanol/DME type having a maximum VOC content of 55%.

The inventors have discovered that this specific combination of polymers constitutes an agent for coating keratin substances, having at the same time good cosmetic properties in particular as regards the feel and the disentangling, good film-forming properties, satisfactory mechanical properties for fixing the hair, good properties of adhesion to the eyelashes and the eyebrows and satisfactory mechanical properties for coating the nails.

After application to the keratin support and drying, a deposit of a composite material is obtained, the structure of which is a continuous hydrophilic material formed by the filmified oligomer, the matrix containing a plurality of rigid nodules comprised of the non-film-forming nanometric particles.

Depending on the respective proportions of the film-forming oligomer and of the rigid, non-filmifiable (non-film-forming) particles, cosmetic hair compositions may be prepared having good lacquering power, good resistance to moisture by reducing the effect of stickiness by hydroscopicity which the hydrophilic oligomer may impart, and good elimination on washing on account of the hydrophilic nature of the continuous matrix of the composite deposit.

The combination in accordance with the present invention also makes it possible to prepare products for coating the eyelashes and the eyebrows, in particular cream mascaras and waterproof mascaras, which have a good power of adhesion to the eyelashes and the eyebrows, are free of any effect of surface stickiness of the film and can easily be eliminated on washing with a make-up remover with a low surfactant content.

The combination in accordance with the invention also makes it possible to prepare nail make-up and/or care products having good adhesion to the nail, good hardness and good rigidity. Furthermore, they can be entirely removed with water or in the presence of a make-up remover with a low surfactant content.

The cosmetic or dermatological compositions in accordance with the invention are characterized in that they comprise, in a cosmetically acceptable aqueous medium:

(A) at least one film-forming oligomer having a molecular weight, preferably measured by steric exclusion chromatography, of less than or equal to 50,000, said at least one film-forming oligomer being soluble or dispersible in said cosmetically acceptable aqueous medium; and (B) rigid, non-film-forming particles of average size less than or equal to 1 μm, said rigid, non-film-forming particles being dispersed in said cosmetically acceptable aqueous medium.

The oligomers of the compositions according to the invention preferably have a molecular weight, measured by steric exclusion chromatography, ranging from 500 to 45,000.

The oligomers of the compositions according to the invention preferably have a glass transition temperature T'g ranging −50° C. to +50° C. and is more preferably from −30 to +40° C. They are preferably soluble in aqueous or aqueous-alcoholic media.

For example, the oligomers in the compositions according to the invention may be nonionic, such as vinylpyrrolidone/vinyl acetate copolymers. They may be amphoteric, for instance N-octylacrylamide/methyl methacrylate/hydroxypropyl methacrylate/acrylic acid/ t-butylaminoethyl methacrylate copolymers such as the product sold under the name Amphomer by the company National Starch. They may also be anionic.

The oligomers particularly preferred are anionic oligomers containing monomers bearing ionized or ionizable anionic groups, in particular carboxylic acid groups and/or sulphonic acid groups. These groups are preferably partially or totally neutralized in order to obtain better solubility of the oligomer in the aqueous medium of the composition and better elimination on washing.

Among the anionic oligomers used according to the invention, mention may be made of copolymers of vinyl esters such as vinyl acetate, vinyl propionate, vinyl neodecanoate and substituted or unsubstituted vinyl benzoates, with a monomer of the maleic acid or crotonic acid type. Mention may be made in particular of the vinyl acetate/ crotonic acid copolymer of identical composition to the product Luviset CA66 sold by the company BASF, but of molecular weight less than or equal to 50,000.

Mention may also be made of copolymers of $C_1$–$C_8$ (meth)acrylic acid esters such as, for example, tert-butyl acrylate, ethyl acrylate, methyl methacrylate and isobutyl acrylate, with the acrylic acid monomer and/or the methacrylic acid monomer. An ethyl acrylate/tert-butyl acrylate/ methacrylic acid copolymer of composition identical to the product sold under the name Luvimer 100 P by BASF, but of molecular weight less than or equal to 50,000, may be used for example.

The film-forming oligomers according to the invention may be prepared conventionally by radical polymerization or copolymerization in solution, suspension or in emulsion.

The film-forming oligomers according to the invention are preferably prepared in solution in an organic solvent, starting with the monomer or monomers as a mixture in the solvent in the presence of a free-radical initiator. They can then be purified by precipitation from a solvent such as petroleum ether.

The process may also be carried out semi-continuously using a base stock containing only the solvent part, a small part of the monomer mixture and part of the initiator. The mixture is then heated to the reaction temperature and the rest of the monomer mixture and the rest of the initiator dissolved in an amount of solvent are then run in simultaneously as two flows.

In the case of anionic oligomers, the oligomers thus obtained may then be partially or totally neutralized with a non-volatile monobasic compound such as an inorganic base, for instance sodium hydroxide or potassium hydroxide, or an amino alcohol taken, for example, from the group selected from 2-amino-2-methyl-1-propanol (AMP), triethanolamine, triisopropanolamine (TIPA), monoethanolamine, 1-tris[(2-hydroxy)propyl]amine, 2-amino-2-methyl-1,3-propanediol (AMPD) and 2-amino-2-hydroxymethyl-1,3-propanediol.

The average size of the rigid, non-film-forming particles of the invention is less than 1 μm, preferably less than 500 nm, still more preferably less than 300 nm and even more preferably less than 100 nm.

The rigid non-film-forming particles used according to the present invention are preferably particles of polymer having a glass transition temperature of higher than 50° C. and more preferably of higher than 70° C.

The size polydispersity of the polymer particles dispersed in the medium of the compositions of the invention, measured by quasi-elastic light scattering, is preferably less than 0.35.

The rigid, non-film-forming polymer particles of the invention preferably are comprised of crosslinked polymer.

The crosslinking agents are preferably chosen from those commonly used in radical polymerization. Mention may be made, for example, of diacrylates or dimethacrylates of ethylene glycol, of polyethylene glycol or of propylene glycol, divinylbenzene, or pentaerythritol di- or trimethacrylate; diacrylates or dimethacrylates of alkylene diols such as hexanediol dimethacrylate. The cross-linking agents are used in amounts preferably ranging from 0.1 to 50% by weight relative to the weight of the monomers constituting the polymer of the latex.

In aqueous media containing volatile organic compounds, in particular those present in the aerosol lacquers or the pump-dispensers of the invention, a dispersion of polymer particles containing ionized or ionizable anionic groups, in particular carboxylic acid or sulphonic acid groups, is preferably used, in order to impart good stabilization to the latex (in particular in an aqueous-alcoholic medium).

These acidic groups are preferably present in amounts less than or equal to 10% by weight, more preferably less than or equal to 8% by weight and even more preferably ranging from 3 to 8% by weight relative to the weight of the polymer.

These acidic groups are preferably partially or totally neutralized with a volatile inorganic base or an amino alcohol as defined above.

Among the polymers constituting the rigid, non-film-forming particles of the invention, mention may be made, for example, of the polymers or copolymers, that are preferably crosslinked, obtained by polymerization or copolymerization of a monomer or of a mixture of monomers chosen from the group consisting of $C_1$–$C_{10}$ linear, cyclic or branched alkyl acrylates or methacrylates, such as methyl methacrylate, tert-butyl methacrylate, cyclohexyl methacrylate, and isobornyl acrylate or methacrylate; styrene;

vinyltoluene; vinyl chloride, vinyl benzoate and vinyl tert-butylbenzoate; acrylic acid and methacrylic acid.

The polymers particularly preferred are crosslinked copolymers of at least one $C_1$–$C_8$ linear, cyclic or branched alkyl methacrylate and of acrylic acid and/or methacrylic acid.

The polymer particle dispersions or "latex" according to the invention may be obtained by batchwise emulsion polymerization, according to a process comprising the steps of:

a) preparing a base stock in the reactor containing water, optionally a buffer and an emulsifier;

b) adding the monomers to the base stock, at room temperature;

c) emulsifying the monomers; and d) heating the reaction medium to the polymerization temperature in the presence of a radical initiator.

The process can also be performed in a semi-continuous manner using a base stock containing only the aqueous part, a small part of the monomer mixture and part of the initiator. The mixture is then heated to the reaction temperature and the rest of the monomer mixture and the rest of the initiator dissolved in an amount of water is then added simultaneously as two flows.

The cosmetically acceptable aqueous medium of the invention preferably comprises water or a mixture of water and at least one cosmetically acceptable solvent which is compatible with the rigid, non-film-forming latex and the film-forming oligomer, such as a monoalcohol, a polyalcohol, a glycol ether, acetone or an ester, alone or in the form of a mixture. It more preferably comprises water or water and a $C_1$–$C_4$ lower alcohol such as ethanol or isopropanol.

The organic solvent concentration in the composition of the invention preferably ranges from 15 to 35% by weight, and more preferably from 20 to 30% by weight relative to the total weight of the composition.

When the composition according to the invention is packaged under pressure in an aerosol device in order to obtain a lacquer, it comprises at least one propellant which may be chosen from volatile hydrocarbons such as n-butane, propane, isobutane, pentane, chloro- and/or fluorohydrocarbons and mixtures thereof; carbon dioxide, nitrous oxide, dimethyl ether, nitrogen or compressed air. The concentration of propellant gas in the aerosol device depends on the nature of the propellant selected.

Dimethyl ether is particularly preferred. It is used in the aerosol lacquers of the invention as a propellant gas in concentrations preferably ranging from 30 to 45% by weight relative to the total weight of the composition.

The concentration of volatile organic compound (VOC) in a composition according to the invention packaged in aerosol or pump-dispenser form is preferably less than or equal to 55% by weight and more preferably ranges from 30 to 55% by weight relative to the total weight of the formulation packaged as an aerosol or as a pump-dispenser.

The pH of the compositions according to the invention preferably ranges from 2 to 9 and more preferably from 3 to 8. It may be adjusted to the selected value by means of basifying or acidifying agents usually used in cosmetics.

In the mixture comprising the rigid, non-film-forming particles and the at least one film-forming oligomer, the concentration of particles preferably range from 5 to 95% by weight of solids relative to the weight of the mixture.

These proportions vary as a function of the intended application of the composition.

When the compositions of the invention are in aerosol lacquer or pump-dispenser form, the concentration of solids content of the rigid, non-film-forming particles preferably ranges from 5 to 60% by weight and those of the at least one oligomer preferably range from 40 to 95% by weight relative to the weight of the particles/oligomer mixture.

The composite material obtained after application and drying on a keratin support comprises a continuous matrix of filmified oligomer containing a plurality of rigid nanometric particles which serve to increase the rigidity of the matrix.

When the compositions of the invention are in aerosol lacquer or pump-dispenser form with a high solids content, it is also possible to use a mixture comprising a high concentration of solids content of rigid, non-film-forming particles, preferably ranging from 70 to 95% by weight relative to the weight of the particles/oligomer mixture.

This specific embodiment of the invention makes it possible to obtain after application a composite material, mainly consisting of a matrix of rigid particles adhesively bonded to each other by the film-forming oligomer, which has good lacquering power on the hair.

This embodiment allows the viscosity of the liquid in the spray device to be optimized by using lower oligomer concentrations while at the same time obtaining good lacquering power.

The compositions according to the invention may in addition optionally include a plasticizer in order to improve the mechanical properties, the cosmetic properties and the adhesion to keratin substances of the composite material deposited after application and drying. In contrast with standard lacquering formulations, the presence of a plasticizer is not obligatory in order to adjust the lacquering power in lacquering formulations of the invention Among the plasticizers which can be used according to the invention, mention may be made of:

Carbitols from the company Union Carbide, namely Carbitol or diethylene glycol ethyl ether, methyl Carbitol or diethylene glycol methyl ether, butyl Carbitol or diethylene glycol butyl ether or hexyl Carbitol or diethylene glycol hexyl ether, Cellosolves from the company Union Carbide, namely Cellosolve or ethylene glycol ethyl ether, butyl Cellosolve or ethylene glycol butyl ether or hexyl Cellosolve or ethylene glycol hexyl ether, propylene glycol derivatives and in particular propylene glycol phenyl ether, propylene glycol diacetate, dipropylene glycol butyl ether, tripropylene glycol butyl ether, and Dowanols from the company Dow Chemical, namely Dowanol PM or propylene glycol methyl ether, Dowanol DPM or dipropylene glycol methyl ether and Dowanol TPM or tripropylene glycol methyl ether.

Mention may also be made of:

diethylene glycol methyl ether or Dowanol DM from the company Dow Chemical, castor oil oxyethylenated with 40 mol of ethylene oxide, such as that sold by the company Rhône-Poulenc under the name "Mulgofen LE-719", benzyl alcohol, triethyl citrate sold by the company Pfizer under the name "Citroflex-2", 1,3-butylene glycol, diethyl, dibutyl and diisopropyl phthalates and adipates, diethyl and dibutyl tartrates, diethyl, dibutyl and 2-diethylhexyl phosphates, and glycerol esters such as glyceryl diacetate (diacetin) and glyceryl triacetate (triacetin).

If included in the composition, the plasticizer is present in a concentration preferably ranging up to 20% by weight relative to the weight of the mixture consisting of the film-forming oligomer and the non-filmifiable particles. This concentration varies according to the intended application.

One subject of the invention relates to the use of the combination comprising an aqueous dispersion of rigid, non-film-forming particles and of the film-forming oligomer according to the invention as defined above as an agent for coating keratin substances, in and for the preparation of a cosmetic or dermatological composition.

The compositions according to the invention as defined above may be used as hair product base for shaping and/or maintaining the hairstyle, in particular aerosol lacquers or pump-dispensers for fixing the hair, lotions for styling or blow-drying, and styling mousses.

The compositions in accordance with the present invention for maintaining the hairstyle preferably include the mixture comprising the rigid, non-film-forming particles and the at least one film-forming oligomer in concentrations ranging from 3 to 20% solids by weight relative to the total weight of the composition.

The hair compositions in accordance with the invention may also include conventional cosmetic additives such as preserving agents, softeners, sequestering agents, fragrances, dyes, viscosity modifiers, pearlescent agents, moisturizers, antidandruff agents, anti-seborrhoeic agents, sunscreens, hair conditioners, antioxidants, proteins and vitamins.

The compositions according to the present invention may be used as an aqueous product base for coating the eyelashes and the eyebrows, such as a mascara, in particular a "cream" mascara or a waterproof mascara.

The compositions in accordance with the present invention for coating the eyelashes and the eyebrows include the combination of the invention as defined above in proportions preferably ranging from 2 to 15% solids by weight relative to the total weight of the composition. The cosmetically acceptable aqueous medium is preferably water or an aqueous-alcoholic medium.

The compositions in accordance with the present invention for coating the eyelashes and the eyebrows preferab include at least one wax.

The waxes used in the mascara compositions according to the invention are chosen from solid, rigid waxes of animal, plant, mineral or synthetic origin and mixtures thereof.

Among the animal waxes which may be mentioned are beeswax, lanolin wax and Chinese waxes.

Among the plant waxes which may be mentioned in particular are rice wax, carnauba wax, candelilla wax, ouricurry wax, cork fibre wax, sugarcane wax, Japan wax and sumac wax.

Among the mineral waxes which may be mentioned in particular are montan wax, microcrystalline waxes, paraffins and ozocerite.

Among the synthetic waxes which may be mentioned in particular are polyethylene waxes, waxes obtained by Fisher-Tropsch synthesis and waxy copolymers, as well as esters thereof.

The waxes obtained by catalytic hydrogenation of animal or plant oils having $C_8$–$C_{32}$ linear or branched fatty chains may also be used in the mascara compositions according to the invention.

Among the latter, mention may be made in particular of hydrogenated jojoba oil, hydrogenated sunflower oil, hydrogenated castor oil, hydrogenated coconut oil and hydrogenated lanolin oil.

The mascara compositions according to the invention may also contain pigments.

These pigments may be organic or inorganic or may also be pearlescent pigments. Such pigments are well known and are described in particular in FR 83/09997 (2,528,699), the disclosure of which is specifically incorporated by reference herein.

The mascara compositions according to the invention may be in various forms. In particular, they may be in the form of oil-in-water or water-in-oil emulsions or in the form of dispersions.

The mascara compositions according to the invention may also contain at least one surfactant selected from anionic surfactants and nonionic surfactants.

Among the anionic surfactants which may be used, along or as a mixture, mention may be made in particular of alkaline salts, ammonium salts, amine salts or amino alcohol salts of the following compounds:

alkyl sulphates, alkyl ether sulphates, alkylamide sulphates, ether sulphates, alkylarylpolyether sulphates, monoglyceride sulphates, alkyl sulphonates, alkylamide sulphonates, alkylaryl sulphonates, α-olefin sulphonates, paraffin sulphonates, alkyl sulphosuccinates, alkyl ether sulphosuccinates, alkylamide sulphosuccinates, alkyl sulphosuccinamates, alkyl sulphoacetates, alkylpolyglyceryl carboxylates, alkyl phosphates/alkyl ether phosphates, alkyl sarcosinates, alkylpolypeptidates, alkylamidopolypeptidates, alkyl isethionates and alkyl taurates.

The term "alkyl" used above is understood to refer to a hydrocarbon chain generally having from 12 to 18 carbon atoms.

Anionic surfactants which can be used in the compositions according to the invention may also be made of fatty acid salts, such as those of oleic, ricinoleic, palmitic and stearic acids, acids of coconut oil or of hydrogenated coconut oil, and in particular the amine salts such as amine stearates.

As anionic surfactants, mention may also be made of acyl lactylates in which the acyl radical comprises from 8 to 20 carbon atoms, and carboxylic acids of polyglycol ethers corresponding to the formula:

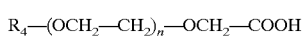

wherein:

$R_4$ represents a linear alkyl radical having from 12 to 18 carbon atoms;

n is an integer ranging from 5 to 15; and the salts of the acids.

Amine stearates are preferably used as anionic surfactant.

Among the nonionic surfactants which may be used, alone or as a mixuture, in the mascara compositions according to the ivention, mention may be made in particular of polyethoxylated, polypropoxylated or polyglycerolated alcohols, alkylphenols and fatty acids containing a fatty chain having from 8 to 18 carbon atoms.

As nonionic surfactants, mention may also be made of copolymers of ethylene oxide and of propylene oxide, condensates of ethylene oxide and of propylene oxide on fatty alcohols, polyethoxylated fatty amides, polyethoxylated fatty amines, ethanolamides, fatty acid esters of glycol, fatty acid esters of sorbitan, which may or may not be oxyethylenated, fatty acid esters of sucrose, fatty acid esters of polyethylene glycols, phosphoric triesters and fatty acid esters of glucose derivatives.

As nonionic surfactants, mention may also be made of the products of condensation of a monoalcohol, an α-diol, an alkylphenol, an amide or a diglycolamide with glycidol or a glycidol precursor as described in patent FR 71/17206 (2,091,516), the disclosure of which is specifically incorporated by reference herein, of formula:

wherein:

$R_5$ represents an aliphatic, cycloaliphatic, or arylaliphatic radical preferably having between 7 and 21 carbon atoms, it being possible for the aliphatic chains to contain ether, thioether or hydroxymethylene groups; and p is an integer ranging from 1 to 10.

As nonionic surfactants, mention may also be made of the compounds described in patent FR 1,477,048, the disclosure of which is specifically incorporated by reference herein, of formula:

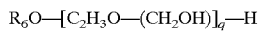

wherein:

$R_5$ represents an alkyl, alkenyl or alkylaryl radical; and q is a random value ranging from 1 to 10.

Mention may also be made of the compounds described in French patent FR 76/31975 (2,328,763), the disclosure of which is specifically incorporated by reference herein, of formula:

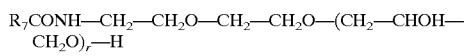

wherein:

$R_7$ represents a saturated or unsaturated linear or branched aliphatic radical which may optionally contain one or more hydroxyl group(s), having between 8 and 30 carbon atoms, of natural or synthetic origin; and r is an integer or fraction ranging from 1 to 5 and denotes the average degree of condensation.

The mascara compositions according to the invention may also comprise at least one conventional additive chosen from a softener, a preserving agent, a sequestering agent, a fragrance, a thickener, an oil, a silicone, a cohesion agent, a basifying agent, an acidifying agent and a filler.

The thickeners which can be used in the mascara compositions according to the invention may be of natural or synthetic origin.

Among the thickeners of synthetic origin which may be mentioned in particular are water-soluble cellulose derivatives, cellulose ether derivatives possessing quaternary ammonium groups, starch derivatives, cationic polysaccharides, acrylic or methacrylic polymer salts, polyenes and polysiloxanes. The mascara compositions according to the invention may also be thickened by addition of a mixture of polyethylene glycol and polyethylene glycol stearate and/or distearate or a mixture of phosphoric esters and fatty amides.

Among the fillers which can be used in the mascara compositions according to the invention, mention may be made in particular of those described in FR 91/10791 (2,680,681), the disclosure of which is specifically incorporated by reference herein.

The mascara compositions for coating the eyelashes in accordance with the invention adhere well to the eyelash, are free of any surface stickiness of the film and are easily removed using an aqueous make-up remover containing a small amount of surfactants.

Another subject of the invention is the compositions according to the invention as an aqueous product base for coating the nails which are easily and completely removed simply by washing the hands with water, without the need to use any make-up remover with a high concentration of surfactant, nor even hot water and/or strongly soapy water.

The nail compositions according to the invention may be used as undercoat for a standard solvent nail varnish, as an aqueous varnish which is easy to remove or as a nail care base containing, in solution or in dispersion in the aqueous medium of the composition, active agents such as nail care protecting agents and/or hardeners.

When the nail composition according to the invention is used as an undercoat for solvent varnish, it is observed that the nail does not tend to become coloured when the solvent varnish is subsequently applied, as is the case in the state of the art; this is due to the fact that the nail is not in direct contact with the varnish.

The nail compositions according to the invention may further comprise at least one pigment. When pigments are introduced into the nail compositions, the nail compositions may be used as varnish.

In the specific mode of use as a nail care product, it may be envisaged to apply the base containing the active agents onto the nail in the evening, allowing the nail to be treated overnight, and then removing this base in the morning by simply washing the hands.

Among the active agents which can be used, mention may be made of vitamins and derivatives thereof; starting materials of biological origin and derivatives thereof such as keratin, proteins, hydrolysates, chitosan, melanin, trace elements and collagen; glycerol; phospholipids; urea; formaldehyde.

The nail compositions according to the invention contain the combination of rigid, non-film-forming particles and at least one film-forming oligomer in a concentration preferably ranging from 15 to 30% solids by weight relative to the total weight of the composition.

Another subject of the invention is a process for the non-therapeutic treatment of keratin substances such as the hair, the eyelashes or the nails, characterized in that it consists in applying a cosmetic composition as defined above directly onto the keratin substances.

The examples which follow serve to illustrate the invention without, however, being limiting in nature.

EXAMPLES

Example 1

Preparation of a Compatible Non-Film-Forming Acrylic Latex in a Water/Ethanol/DME Aerosol Lacquer Medium with a Maximum VOC Content of 55%

Composition of the Polymer of the Latex:

| | |
|---|---|
| methyl methacrylate | 91% by weight |
| methacrylic acid | 5% by weight |
| ethylene glycol dimethacrylate (cross-linking agent) | 4% by weight |

Procedure:

The following mixture was introduced into a cylindrical reactor with central mechanical stirring, a thermometer and a condenser, while sparging with nitrogen:

| | |
|---|---|
| deionized water | 28 g |
| NaHCO$_3$ | 0.7 g |
| nonylphenolpolyoxyethylene (containing 25 oxyethylene units) and sulphated at the end of the chain, sold under the name AD 33 by the company Seppic | 6.56 g |

The mixture was dissolved with stirring and while sparging with nitrogen. The monomer mixture made up as below was then added, with stirring and at room temperature:

| | |
|---|---|
| methyl methacrylate | 91 g |
| methacrylic acid | 5 g |
| ethylene glycol dimethacrylate (cross-linking agent) | 4 g |

The monomers were emulsified at 250 revolutions/minute while sparging with nitrogen. This emulsion was brought to 72° C. and the initiator, that is to say: 0.5 g of potassium persulphate dissolved in 20 g of deionized water, was added at this temperature.

The mixture was left to react under these conditions at 72° C. for 3 hours and the temperature was then raised to 85° C. and the reaction was continued for a further 5 hours.

The mixture was then cooled to room temperature with stirring. The latex was recovered and was filtered.

A stable latex with a polymer solids concentration equal to 25% by weight was obtained.

The Tg temperature measured by DSC (differential scanning calorimetry) was 115° C.

The particle sizes were determined by quasi-elastic light scattering on a Coulter N4 SD machine from the company Coultronix:

| | |
|---|---|
| average particle size | 65 nm |
| size polydispersity | <0.1 |

Example 2

Preparation of a Compatible Film-Forming Acrylic Oligomer in a Water/Ethanol/DME Aerosol Lacquer Medium with a Maximum VOC Content of 55%

Composition of the Oligomer:

| | |
|---|---|
| isobutyl acrylate | 50% by weight |
| tert-butyl acrylate | 40% by weight |
| acrylic acid | 10% by weight |

Procedure:

The following mixture was introduced into a cylindrical reactor with central mechanical stirring, a thermometer and a condenser, while sparging with nitrogen:

| | |
|---|---|
| isobutyl acrylate | 50 g |
| tert-butyl acrylate | 40 g |
| methacrylic acid | 10 g |
| azobisisobutylacrylonitrile (initiator) | 2 g |
| ethanol | 200 g |

The mixture was brought to the reflux point of ethanol (78° C.) with stirring, while sparging with nitrogen. It was left to react for 12 hours under these conditions. It was cooled to room temperature. The polymer was then purifed by precipitation of the alcoholic solution from 5 l of petroleum ether. The precipitate was then dried until a constant weight was obtained.

The yield obtained after drying was 90%. The acid number obtained was 81.5. The peak height molecular weight measured by steric exclusion chromatography was 36,800 (elution in tetrahydrofuran relative to polystyrene standards). The T'g temperature measured by DSC was 27° C.

A concentrated alcoholic solution of oligomer 100% neutralized with 2-amino-2-methyl-1-propanol (AMP) was prepared from the following mixture:

| | |
|---|---|
| oligomer of Example 2 | 100 g |
| AMP | 12.44 g |
| ethanol | 112.44 g |

The mixture was stirred for 24 hours at room temperature. A solution containing 50% oligomer solids by weight was obtained.

Example 3

Preparation of a Compatible Film-Forming Acrylic Oligomer in a Water/Ethanol/DME Aerosol Lacquer Medium with a Maximum VOC Content of 55%

Composition of the Oligomer:

| | |
|---|---|
| isobutyl acrylate | 90% by weight |
| acrylic acid | 10% by weight |

Procedure:

The following mixture was introduced into a cylindrical reactor with central mechanical stirring, a thermometer and a condenser, while sparging with nitrogen:

| | |
|---|---|
| isobutyl acrylate | 90 g |
| acrylic acid | 10 g |
| azobisisobutylacrylonitrile (initiator) | 2 g |
| ethanol | 200 g |

The process was performed under the same conditions as those of Example 2.

The yield obtained after drying was 95%. The acid number obtained was 81. The peak height molecular weight measured by steric exclusion chromatography was 33,400 (elution in tetrahydrofuran relative to polystyrene standards). The T'g temperature measured by DSC was 0° C.

A concentrated alcoholic solution of oligomer 100% neutralized with 2-amino-2-methylpropanol (AMP) was prepared from the following mixture:

| | |
|---|---|
| oligomer of Example 3 | 100 g |
| AMP | 12.44 g |
| ethanol | 112.44 g |

The mixture was stirred for 24 hours at room temperature. A oligomer solution containing 50% solids was thus obtained.

Example 4

Preparation of a Compatible Film-Forming Oligomer in a Water/Ethanol/DME Aerosol Lacquer Medium with a Maximum VOC Content of 55%

Composition of the Oligomer:

| | |
|---|---|
| crotonic acid | 10% by weight |
| vinyl acetate | 90% by weight |

Procedure:

The following mixture was introduced successively into a cylindrical reactor with central magnetic stirring, a thermometer and a condenser, while sparging with nitrogen, so as to make up the "base stock":

| | |
|---|---|
| crotonic acid | 1 g |
| vinyl acetate | 9 g |
| ethyl acetate | 80 g |
| tert-butyl 2-peroxyethylhexanoate sold under the name Trigonox 21 S by the company Akzo | 0.7 g |

The mixture was brought to 78° C. (reflux) with stirring and sparging, and was left to react for 15 minutes. The rest of the monomer mixture, on the one hand, and of the initiator dissolved in the rest of the solvent, on the other hand, were then simultaneously added as two flows. For this, the monomer mixture made up as below was introduced in a first addition funnel:

| | |
|---|---|
| crotonic acid | 9 g |
| vinyl acetate | 81 g |

This mixture was run into the reaction medium with stirring and at reflux for 4 hours. Simultaneously, the mixture made up as below was introduced in a second addition funnel:

| | |
|---|---|
| ethyl acetate | 80 g |
| tert-butyl 2-peroxyethylhexanoate sold under the name Trigonox 21 S by the company Akzo | 2 g |

This second mixture was run into the reaction medium over 4 h 30, at the same time as the first mixture.

At the end of the two additions, the mixture was left to react for a further 2 hours at reflux. The rest of the initiator in the solvent was then finally run in. For this, the mixture made up as below was introduced in an addition funnel:

| | |
|---|---|
| ethyl acetate | 30 g |
| tert-butyl 2-peroxyethylhexanoate sold under the name Trigonox 21 S by the company Akzo | 1 g |

This mixture was added to the medium over 1 hour with stirring and at reflux.

The mixture was left to react for a further 4 hours after the end of the introduction. It was then cooled to room temperature and the polymer was purified by precipitating the solution from 10 l of petroleum ether. The precipitate was dried until a constant weight was obtained.

| | |
|---|---|
| Yield: | 76.2% |
| Acid number: (i.e. 11.7% crotonic acid) | 75.9% |
| Temperature T'g measured by DSC: | 40° C. |
| Molecular weight measured by steric exclusion chromatography | 23,000 |

Example 5

Water/Ethanol/DME Aerosol Lacquer Containing 55% VOC for Fixing Hair, Containing a Mixture Consisting of 30% Rigid, Non-Film-Forming Latex Solids by Weight and 70% Oligomer Solids by Weight

COMPOSITION BEFORE PACKAGING:

| | |
|---|---|
| Alcoholic solution containing 50% of oligomer of Example 2 by weight | 166.70 g |
| Deionized water | 854.87 g |
| Ethanol | 395.72 g |
| Dispersion containing 25% non-film-forming particles of Example 1 by weight | 100.00 g |

AEROSOL LACQUER CONTAINING 55% VOC:

| | |
|---|---|
| Above composition | 35 g |
| Dimethyl ether | 15 g |

This lacquer contained 5% solids by weight

After application to the hair, excellent lacquering power, good cosmetic properties and good removal of the deposit on shampooing were obtained.

Example 6

Water/Ethanol/DME Aerosol Lacquer Containing 55% VOC for Fixing Hair, Containing a Mixture Consisting of 50% Rigid, Non-Film-Forming Latex Solids by Weight and 50% Oligomer Solids by Weight

COMPOSITION BEFORE PACKAGING:

| | |
|---|---|
| Alcoholic solution containing 50% oligomer of Example 2 by weight | 50.00 g |
| Deionized water | 354.18 g |
| Ethanol | 196.10 g |
| Dispersion containing 25% non-film-forming particles of Example 1 by weight | 100.00 g |

AEROSOL LACQUER CONTAINING 55% VOC:

| | |
|---|---|
| Above composition | 35 g |
| Dimethyl ether | 15 g |

This lacquer contained 5% solids by weight

After application to the hair, excellent lacquering power, good cosmetic properties and complete removal of the deposit on shampooing were obtained.

Example 7

Water/Ethanol/DME Aerosol Lacquer Containing 55% VOC for Fixing the Hair, Containing a Mixture Consisting of 50% Rigid, Non-Film-Forming Latex Solids by Weight and 50% Oligomer Solids by Weight

COMPOSITION BEFORE PACKAGING:

| | |
|---|---|
| Alcoholic solution containing 50% oligomer of Example 3 by weight | 50.00 g |
| Deionized water | 354.18 g |

-continued

| Ethanol | 196.10 g |
| Dispersion containing 25% non-film-forming particles of Example 1 by weight | 100.00 g |

AEROSOL LACQUER CONTAINING 55% VOC:

| Above composition | 35 g |
| Dimethyl ether | 15 g |

This lacquer contained 5% solids by weight

After application to the hair, excellent lacquering power, good cosmetic properties and complete removal of the deposit on shampooing were obtained.

Example 8

Water/Ethanol/DME Aerosol Lacquer Containing 55% VOC for Fixing the Hair, Containing a Mixture Consisting of 50% Rigid, Non-Film-Forming Latex Solids by Weight and 50% Oligomer Solids by Weight
COMPOSITION BEFORE PACKAGING:

| Oligomer of Example 4 | 3.20 g |
| AMP to 100% neutralize the oligomer | 0.38 g |
| Deionized water | 50.58 g |
| Ethanol | 31.57 g |
| Dispersion containing 25% non-film-forming particles of Example 1 by weight | 14.28 g |

AEROSOL LACQUER CONTAINING 55% VOC:

| Above composition | 35 g |
| Dimethyl ether | 15 g |

This lacquer contained 5% solids by weight

After application to the hair, excellent lacquering power, good cosmetic properties and complete removal of the deposit on shampooing were obtained.

Example 9

Water/Ethanol/DME Aerosol Lacquer Containing 45% VOC for Fixing the Hair, Containing a Mixture Consisting of 50% Rigid, Non-Film-Forming Latex Solids by Weight and 50% Film-Forming Oligomer Solids by Weight
COMPOSITION BEFORE PACKAGING:

| Alcoholic solution containing 50% oligomer of Example 2 by weight | 11.54 g |
| Deionized water | 55.06 g |
| Ethanol | 10.32 g |
| Dispersion containing 25% non-film-forming particles of Example 1 by weight | 23.08 g |

AEROSOL LACQUER CONTAINING 45% VOC:

| Above composition | 65 g |
| Dimethyl ether | 35 g |

This lacquer contained 7.5% solids by weight

After application to the hair, excellent lacquering power, good cosmetic proper ties and complete removal of the deposit on shampooing were obtained.

Example 10

Water/Ethanol/DME Aerosol Lacquer Containing 33.5% VOC for Fixing the Hair, Containing a Mixture Consisting of 75% Rigid, Non-Film-Forming Latex Solids by Weight and 25% Film-Forming Oligomer Solids by Weight
COMPOSITION BEFORE PACKAGING:

| Alcoholic solution containing 50% oligomer of Example 2 by weight | 10 g |
| Deionized water | 30 g |
| Dispersion containing 25% non-film-forming particles of Example 1 by weight | 60 g |

AEROSOL LACQUER CONTAINING 33.5% VOC:

| Above composition | 70 g |
| Dimethyl ether | 30 g |

This lacquer contained 14% solids by weight

After application to the hair, the hair became only very slightly damp, despite the large amount of water contained in the spray, and rapid fixing of the hairstyle, good lacquering power, good pleasant feel and easy disentangling on brushing were obtained. Total removal of the deposit on shampooing was also observed.

We claim:

1. A cosmetic or dermatological composition comprising, in a cosmetically acceptable aqueous medium:
   (a) at least one film-forming oligomer having a molecular weight, measured by steric exclusion chromatography, of less than or equal to 50,000, said at least one film-forming oligomer being soluble or dispersible in said cosmetically acceptable aqueous medium; and
   (b) rigid, non-film-forming particles of average size less than or equal to 1 $\mu$m, said rigid, non-film-forming particles being dispersed in said cosmetically acceptable aqueous medium, wherein said rigid, non-film-forming particles are particles of a crosslinked polymer having a glass transition temperature Tg of higher than 50° C.,
   wherein the concentration of said rigid, non-film-forming particles ranges from 5 to 95% solids, relative to the weight of the mixture of said at least one film-forming oligomer and said non-film-forming particles,
   and further wherein the crosslinked polymer constituting said rigid, non-film-forming particles is polymerized or copolymerized from at least one monomer, wherein the at least one monomer is a $C_1$–$C_{10}$ linear alkyl acrylate, a $C_3$–$C_{10}$ cyclic alkyl acrylate, a $C_1$–$C_{10}$ branched alkyl acrylate, a $C_1$–$C_{10}$ linear alkyl methacrylate, a $C_3$–$C_{10}$ cyclic alkyl methacrylate, a $C_1$–$C_{10}$ branched alkyl methacrylate, styrene, vinyltoluene, vinyl chloride, vinyl benzoate, vinyl tertbutylbenzoate, acrylic acid or methacrylic acid.

2. A composition according to claim 1, wherein said at least one film-forming oligomer has a glass transition temperature T'g ranging from −50° C. to +50° C.

3. A composition according to claim 2, wherein said at least one film-forming oligomer has a glass transition temperature T'g ranging from −30° C. to +40° C.

4. A composition according to claim 1, wherein said cosmetically acceptable aqueous medium is an aqueous medium or an aqueous-alcoholic medium and further wherein said at least one film-forming oligomer is soluble in said aqueous medium or said aqueous-alcoholic medium.

5. A composition according to claim 1, wherein said at least one film-forming oligomer is a nonionic polymer, an anionic polymer or an amphoteric polymer.

6. A composition according to claim 5, wherein said nonionic polymer is a vinylpyrrolidone/vinyl acetate copolymer and wherein said amphoteric polymer is a N-octylacrylamide/methyl methacrylate/hydroxypropyl methacrylate/acrylic acid/t-butylaminoethyl methacrylate copolymer.

7. A composition according to claim 5, wherein said anionic polymer is an anionic polymer bearing ionized anionic groups or an anionic polymer bearing ionizable anionic groups, which may be partially or totally neutralized.

8. A composition according to claim 7, wherein said anionic polymer bears carboxylic acid groups, sulphonic acid groups, or mixtures thereof.

9. A composition according to claim 8, wherein said carboxylic acid groups, sulphonic acid groups, or mixtures thereof are present in a concentration of up to 10% by weight relative to the weight of the oligomer.

10. A composition according to claim 1, wherein said at least one film-forming oligomer is a copolymer of vinyl esters and crotonic acid, a copolymer of vinyl esters and maleic acid, a copolymer of $C_1-C_8$ (meth)acrylic acid esters and acrylic acid, or a copolymer of $C_1-C_8$ (meth)acrylic acid esters and methacrylic acid.

11. A composition according to claim 1, wherein said rigid, non-film-forming particles have an average size of less than or equal to 500 nm.

12. A composition according to claim 11, wherein said rigid, non-film-forming particles have an average size of less than or equal to 300 nm.

13. A composition according to claim 12, wherein said rigid, non-film-forming particles have an average size of less than or equal to 100 nm.

14. A composition according to claim 1, wherein said rigid, non-film-forming particles are particles of polymer having a glass transition temperature Tg of higher than 70° C.

15. A composition according to claim 1, wherein the size polydispersity of said rigid, non-film-forming polymer particles, measured by quasi-elastic light scattering, is less than 0.35.

16. A composition according to claim 1, wherein a residue of a crosslinking agent is present in a concentration ranging from 0.1 to 50% by weight relative to the weight of said polymer.

17. A composition according to claim 1, wherein said polymer constituting said rigid, non-film-forming particles is a crosslinked copolymer of a) at least one $C_1-C_8$ linear, cyclic or branched alkyl methacrylate and b) acrylic acid, methacrylic acid, or a mixture thereof.

18. A composition according to claim 1, wherein said cosmetically acceptable aqueous medium comprises water or a mixture of water and at least one cosmetically acceptable solvent which is compatible with said rigid, non-film-forming particles and said at least one film-forming oligomer.

19. A composition according to claim 18, wherein said at least one cosmetically acceptable solvent is a monoalcohol, a polyalcohol, a glycol ether, acetone, an ester, or a mixture thereof.

20. A composition according to claim 18, wherein said aqueous medium comprises water and a $C_1-C_4$ lower alcohol.

21. A composition according to claim 18, wherein said at least one cosmetically acceptable solvent is present in a concentration ranging from 15 to 35% by weight relative to the total weight of the composition.

22. A composition according to claim 21, wherein said at least one cosmetically acceptable solvent is present in a concentration ranging from 20 to 30% by weight relative to the total weight of the composition.

23. A composition according to claim 1, wherein said composition is packaged in an aerosol device under pressure or a pump-dispenser.

24. A composition according to claim 23, wherein said composition is packaged in an aerosol device under pressure in the presence of at least one propellant.

25. A composition according to claim 24, wherein said at least one propellant is a volatile hydrocarbon, a chlorohydrocarbon, a fluorohydrocarbon, or a mixture thereof; carbon dioxide, nitrous oxide, dimethyl ether, nitrogen or compressed air.

26. A composition according to claim 25, wherein said at least one propellant is dimethyl ether.

27. A composition according to claim 26, wherein said dimethyl ether is present in a concentration ranging from 30 to 45% by weight relative to the total weight of the composition.

28. A composition according to claim 23, wherein the concentration of any volatile organic compound (VOC) present is less than or equal to 55% by weight relative to the total weight of the composition packaged as an aerosol or as a pump-dispenser.

29. A composition according to claim 28, wherein the concentration of volatile organic compound (VOC) ranges from 30 to 55% by weight relative to the total weight of the composition packaged as an aerosol or as a pump-dispenser.

30. A composition according to claim 1, wherein the pH of said composition ranges from 2 to 9.

31. A composition according to claim 30, wherein the pH of said composition ranges from 3 to 8.

32. A composition according to claim 1, wherein the concentration of said rigid, non-film-forming particles ranges from 40 to 95% solids by weight relative to the weight of the mixture of said at least one film-forming oligomer and said non-film-forming particles.

33. A composition according to claim 32, wherein the concentration of said rigid, non-film-forming particles ranges from 70 to 95% solids by weight relative to the weight of the mixture of said at least one film-forming oligomer and said non-film-forming particles.

34. A composition according to claim 1, wherein the concentration of said rigid, non-film-forming particles ranges from 5 to 60% solids by weight and the concentration of said at least one film-forming oligomer ranges from 40 to 95% solids by weight, relative to the weight of the mixture of said at least one film-forming oligomer and said non-film-forming particles.

35. A composition according to claim 1, wherein said composition further comprises at least one plasticizer.

36. A composition according to claim 35, wherein said at least one plasticizer is present in a concentration up to 20% by weight, relative to the weight of said composition.

37. A method for coating a keratin substance comprising the step of applying to said keratin substance the cosmetic or dermatological composition according to claim 1.

38. A hair product base for shaping or maintaining the hairstyle comprising the cosmetic or dermatological composition according claim 1.

39. A hair product for shaping or maintaining the hairstyle, comprising the cosmetic or dermatological composition according to claim 1.

40. A hair product according to claim 39, wherein said at least one film-forming oligomer having a molecular weight, measured by steric exclusion chromatography, of less than or equal to 50,000 and said rigid, non-film-forming particles of average size less than or equal to 1 μm are present in a concentration ranging from 3 to 20% solids by weight relative to the total weight of the cosmetic or dermatological composition.

41. A hair product for shaping or maintaining the hairstyle according to claim 39, wherein said hair product is selected from aerosol lacquers, pump-dispensers for fixing the hair, hairsetting lotions, blow-drying lotions, and styling mousses.

42. A product base for coating the eyelashes and the eyebrows comprising the cosmetic composition according to claim 1.

43. A product for coating the eyelashes and the eyebrows comprising the cosmetic composition according to claim 1.

44. A product base according to claim 42, wherein said product base is contained in a mascara.

45. A product base according to claim 44, wherein said mascara is a cream mascara or a waterproof mascara.

46. A product for coating the eyelashes and the eyebrows according to claim 43, wherein wherein said at least one film-forming oligomer having a molecular weight, measured by steric exclusion chromatography, of less than or equal to 50,000 and said rigid, non-film-forming particles of average size less than or equal to 1 μm are present in a concentration ranging from 2 to 15% solids by weight relative to the total weight of the cosmetic or dermatological composition.

47. A product base for coating the nails comprising the cosmetic composition according to claim 1.

48. A product for coating the nails comprising the cosmetic composition according to claim 1.

49. A product for coating the nails according to claim 48, wherein wherein said at least one film-forming oligomer having a molecular weight, measured by steric exclusion chromatography, of less than or equal to 50,000 and said rigid, non-film-forming particles of average size less than or equal to 1 μm are present in a concentration ranging from 15 to 30% solids by weight relative to the total weight of the cosmetic or dermatological composition.

50. A product for coating the nails according to claim 48, wherein said product for coating the nails is selected from a nail varnish which is easily removed by washing, a nail varnish undercoat, a nail care base comprising protecting agents, and a nail-hardening product.

51. A process for the treatment of a keratin substance comprising the step of applying a cosmetic or dermatological composition according to claim 1 onto the keratin substance.

52. A process according to claim 51, wherein said cosmetic or dermatological composition according to claim 1 is directly applied onto the keratin substance.

53. A process according to claim 52, wherein said keratin substance is selected from hair, eyelashes, eyebrows, and nails.

54. A composition according to claim 2, wherein said at least one film-forming oligomer has a molecular weight, measured by steric exclusion chromatography, ranging from 500 to 45,000.

55. A process according to claim 51, wherein said treatment is non-therapeutic and wherein said composition is cosmetic.

56. A composition according to claim 1, wherein the crosslinked polymer constituting said rigid, non-film-forming particles is an anionic polymer bearing carboxylic acid groups, sulphonic acid groups, or a mixture thereof, said carboxylic acid groups, sulphonic acid groups, or a mixture thereof being present in a concentration of less than or equal to 10% by weight relative to the weight of the polymer.

57. A composition according to claim 56, wherein said acid groups are present in a concentration of less than or equal to 8% by weight relative to the weight of the polymer.

58. A composition according to claim 57, wherein said acid groups are present in a concentration ranging from 3 to 8% by weight relative to the weight of the polymer.

* * * * *